(12) United States Patent
Virji et al.

(10) Patent No.: US 8,961,880 B2
(45) Date of Patent: Feb. 24, 2015

(54) POLYANILINE NANOFIBER-AMINE COMPOSITE MATERIALS FOR PHOSGENE DETECTION

(75) Inventors: Shabnam Virji, Yorba Linda, CA (US); Robert Kojima, Los Angeles, CA (US); Richard B. Kaner, Pacific Palisades, CA (US); Bruce H. Weiller, Santa Monica, CA (US)

(73) Assignees: The Aerospace Corporation, El Segundo, CA (US); The Regents of the University of California, Oakland, CA (US)

( * ) Notice: Subject to any disclaimer, the term of this patent is extended or adjusted under 35 U.S.C. 154(b) by 1391 days.

(21) Appl. No.: 12/173,008

(22) Filed: Jul. 14, 2008

(65) Prior Publication Data

US 2010/0006434 A1  Jan. 14, 2010

(51) Int. Cl.
*G01N 27/00* (2006.01)
*G01N 27/04* (2006.01)

(52) U.S. Cl.
CPC ............. *G01N 27/04* (2013.01); *Y10S 977/953* (2013.01); *Y10S 977/957* (2013.01)
USPC ............... 422/98; 422/83; 204/431; 977/953; 977/957

(58) Field of Classification Search
None
See application file for complete search history.

(56) References Cited

U.S. PATENT DOCUMENTS 4,141,800 A * 2/1979 Breuer et al. ............... 205/779.5
5,928,609 A * 7/1999 Gibson et al. ................. 422/90

OTHER PUBLICATIONS

Virji et al., Direct electrical measurement of the conversion of metal acetates to metal sulfides by hydrogen sulfide, 2006, Inorganic Chemistry, vol. 45, No. 26, p. 10467-10471.*
Kanungo et al., Microtubule sensors and sensor array based on polyaniline synthesized in the presence of poly(styrene sulfonate), 2003, Analytical Chemistry, vol. 75, No. 21, p. 5673-5679.*
Virgi et al., Polyaniline nanofiber gas sensors: examination of response mechanisms, 2004, American Chemical Society, Nano Lett., vol. 4, No. 3, p. 491-496.*
Yang et al., Electrochemical copolymerization of aniline and paraphenylene diamine on IrO2-coated titanium electrode, Hournal of applied electrochemistry, 24 (1994) p. 166-178.*

* cited by examiner

*Primary Examiner* — Paul Hyun
*Assistant Examiner* — Robert Eom
(74) *Attorney, Agent, or Firm* — Koppel, Patrick, Heybl & Philpott; Michael J. Ram

(57) ABSTRACT

A sensor for detecting phosgene includes a pair of electrodes separated by an electrode gap, and a layer of conducting polymer material positioned over and making electrical contact with the pair of electrodes, the layer of conducting polymer material being modified with an amine such that the electrical resistance of the conducting polymer material measured across the electrodes is responsive to changes in an amount of phosgene to which the conducting polymer material is exposed.

26 Claims, 4 Drawing Sheets

Response of polyaniline nanofiber composite films to 2 ppm phosgene at 50% relative humidity and room temperature Response of polyaniline nanofiber composite film to 100 ppb phosgene Interaction of polyaniline nanofiber composite film with phosgene FTIR spectra of polyaniline nanofiber composite film
before and after exposure to phosgene Response of polyaniline nanofiber composite films to 2 ppm phosgene
at 50% relative humidity and room temperature Ethylene Diamine Phenylene Diamine Ethylene Diamine:HCl Phenylene Diamine:HCl Metanilic Acid Chemical Structures of the amines Phosgene sensor and resistance monitor

POLYANILINE NANOFIBER-AMINE COMPOSITE MATERIALS FOR PHOSGENE DETECTION

This invention was made with Government support under grant No.DMR0507294 awarded by the National Science Foundation. The Government has certain rights in this invention.

TECHNICAL FIELD

The invention relates generally to sensors for detecting gases and, in particular, to sensors with amine modified nanofiber composite materials for detecting phosgene.

BACKGROUND ART

Phosgene, $COCl_2$, is a colorless, highly toxic gas which has been used in chemical warfare, notably in World War I, as well as in industrial processes including the making of dyestuffs and polyurethane resins. When inhaled, phosgene reacts with water in the lungs to form hydrochloric acid and carbon monoxide. The release of hydrochloric acid into the lungs causes pulmonary edema and may also cause bronchial pneumonia and lung abscesses, which in severe cases may result in death within 36 hours.

Conducting polymers, such as polyaniline, have been widely studied as chemical sensors due to their simple and reversible acid doping and base dedoping chemistry. Polyaniline is a conducting polymer that has been widely studied for electronic and optical applications. Unlike other conjugated polymers, polyaniline has a simple and reversible acid doping and base dedoping chemistry enabling control over properties such as free-volume, solubility, electrical conductivity, and optical activity. In recent years, one-dimensional polyaniline nanostructures, including nano-wires, rods, and tubes have been studied with the expectation that such materials will possess the advantages of both low-dimensional systems and organic conductors. The change in conductivity associated with the transition from the insulating emeraldine base to the conducting emeraldine salt form of polyaniline is over ten orders of magnitude. This wide range in conductivity has been utilized to make polyaniline sensors that can detect either acids or bases. Polyaniline is one of the most widely studied conducting polymers because of polyaniline's environmental stability and straightforward synthesis. Polyaniline is a useful material for chemical sensors because polyaniline conductivity can change in the presence of doping and dedoping agents. In the undoped state, insulating emeraldine polyaniline is an interesting material for chemical sensors because the conductivity can increase by over ten orders of magnitude on exposure to doping acids. This process can be reversed by dedoping in the presence of bases.

It would be useful to be able to provide a chemical sensor for detecting phosgene using a conductive polymer such as polyaniline and/or a nanofiber material.

SUMMARY OF THE INVENTION

Embodiments described herein utilize amine modified nanofiber composite materials for phosgene detection. The detection mechanism involves the interaction of phosgene with an amine to form a strong acid and an amide. The strong acid then dopes the polyaniline changing its chemical state from emeraldine base to emeraldine salt. This change also results in orders of magnitude changes in resistance. The synthesis of polyaniline nanofiber composite films and their applications as phosgene sensors are also described.

In an example embodiment, a sensor for detecting phosgene includes a pair of electrodes separated by an electrode gap, and a layer of conducting polymer material (e.g., polyaniline material) positioned over and making electrical contact with the pair of electrodes, the layer of conducting polymer material being modified with an amine such that the electrical resistance of the conducting polymer material measured across the electrodes is responsive to changes in an amount of phosgene to which the conducting polymer material is exposed.

In an example embodiment, a sensor for detecting phosgene includes a pair of electrodes separated by an electrode gap, and a polyaniline nanofiber composite material (e.g., in the form of a film) positioned over and making electrical contact with the pair of electrodes, the polyaniline nanofiber composite material being modified with amine additives such that the electrical resistance of the polyaniline nanofiber composite material measured across the electrodes is responsive to changes in an amount of phosgene to which the polyaniline nanofiber composite material is exposed.

DISCLOSURE OF INVENTION

Polyaniline nanofibers suitable for the phosgene sensors described herein can be synthesized, for example, using the interfacial polymerization technique. See, Polyaniline Nanofiber Composites with Metal Salts: Chemical Sensors for Hydrogen Sulfide, Virji, S.; Fowler, J. D.; Baker, C. O.; Huang, J.; Kaner, R. B.; Weiller, B. H., Small 2005, 1(6), 624-627.

In an example embodiment, the nanofibers were modified with amines by adding 0.01 M amine solution to the aqueous polyaniline nanofiber dispersion in a ratio of 1:5 by volume. Suitable amines include, by way of example, ethylene diamine, ethylene diamine dihydrochloride salt, phenylene diamine, phenylene diamine dihydrochloride salt, and metanilic acid. Other water soluble amines can also be used to detect phosgene. In an example embodiment, gold interdigitated electrode sensor arrays with 20 μm electrode gaps were used as the sensor substrates. The films were made by drop-casting the solution on the electrodes and drying the film in air. A Keithley 2002 multimeter was used to measure the sensor electrical resistances. Mass flow controllers directed the flow of calibrated gas mixtures into the cell. A bubbler with water was used to generate humidity that was measured with a humidity sensor.

Occupational Safety and Health Administration (OSHA) sets enforceable Permissible Exposure Limits (PELs) to protect workers against the health effects of exposure to hazardous substances. PELs are regulatory limits on the amount or concentration of a substance in the air. They may also contain a skin designation.

Immediately Dangerous to Life and Health (IDLH) is defined by the National Institute for Occupational Safety and Health (NIOSH) as exposure to airborne contaminants that is "likely to cause death or immediate or delayed permanent adverse health effects or prevent escape from such an environment."

Phosgene is highly toxic and widely used in organic synthesis, with exposure limits of PEL=99 ppb and an IDLH=2 ppm. Unmodified polyaniline cannot detect phosgene at the low exposure limits. The polyaniline nanofiber composite films modified with amine additives as described herein can be used (and have been observed) to detect phosgene at levels lower than the PEL.

Figure 1:
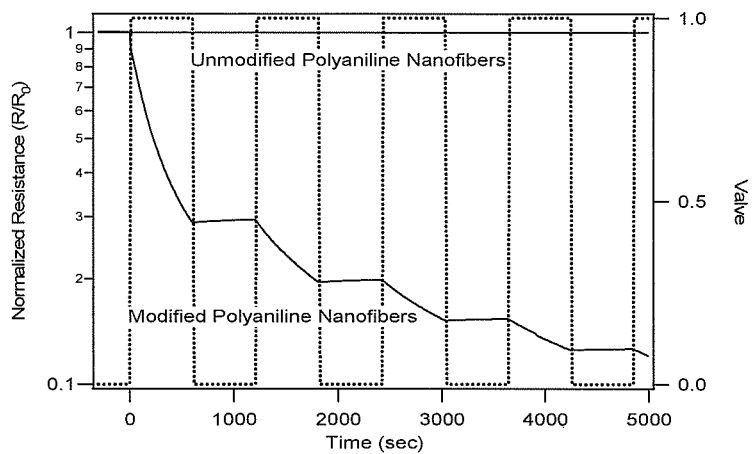
FIG. 1 is a plot showing the response of polyaniline nanofiber composite film to 100 ppb phosgene.
Figure 2:
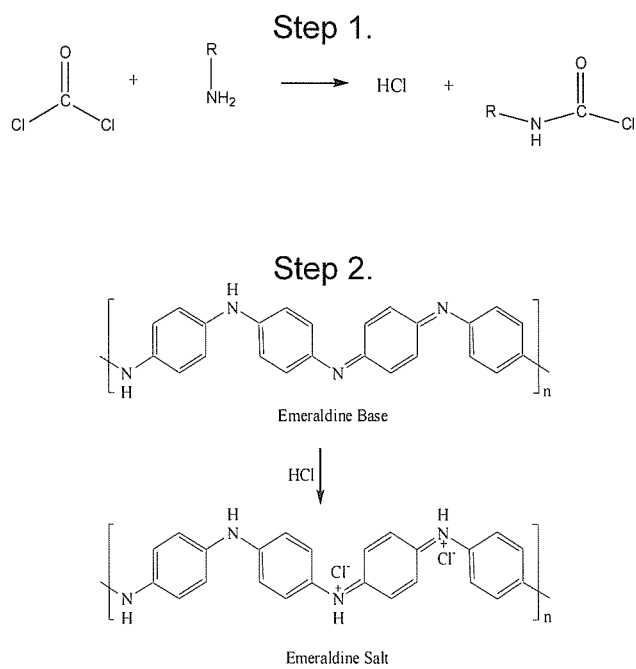
FIG. 2 shows an example mechanism of interaction of polyaniline nanofiber composite film with phosgene.
Figure 3:
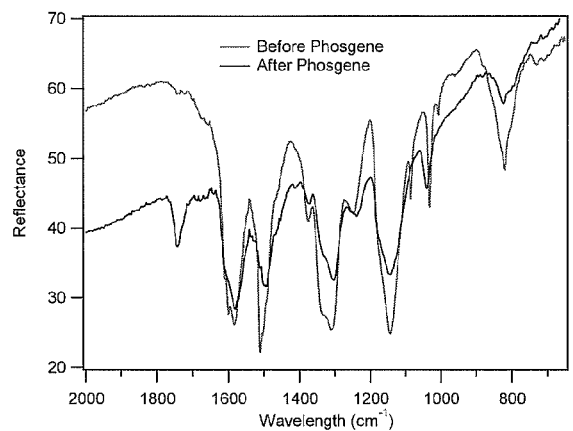
FIG. 3 is a plot showing Fourier Transform Infrared (FTIR) spectra of polyaniline nanofiber composite film before and after exposure to phosgene.

FIG. 1 shows the response curve of the polyaniline nanofiber composite film to phosgene. The data is presented as normalized resistance ($R/R_0$) where $R_0$ is the resistance before gas exposure and R is the time dependent resistance during gas exposure. The valve switching is shown on the right axis with 1 being on and 0 being off. Also shown is the same experiment for a film of unmodified polyaniline nanofibers. As seen from the figure the unmodified polyaniline shows no response to phosgene while the amine modified polyaniline nanofiber shows a decrease in resistance indicative of doping of the polyaniline nanofibers. FIG. 2 shows the response mechanism of the phosgene interacting with an amine to form an amide and HCl, a strong acid. The HCl can then dope the polyaniline causing a resistance decrease in the film as seen in FIG. 1. This mechanism is further shown in the FTIR of the film before and after exposure to phosgene. FIG. 3 shows the FTIR spectra of a polyaniline nanofiber composite film before and after exposure to phosgene. As seen from the figure, there is a new carbonyl peak that forms at 1750 $cm^{-1}$ indicative of the amide reaction product.

Figure 4:
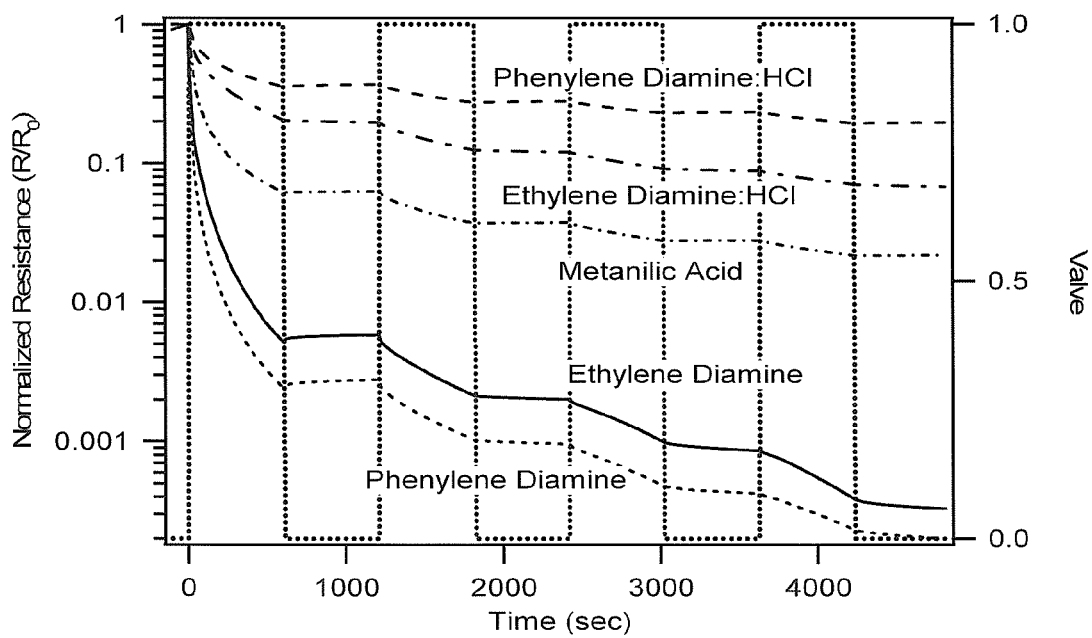
FIG. 4 is a plot showing the response of polyaniline nanofiber composite films to 2 ppm phosgene at 50% relative humidity and room temperature.

FIG. 4 shows the response of various amine modified polyaniline nanofiber composite films exposed to phosgene. As seen from the figure, the different amines give different responses to phosgene. This is influenced by the $pK_a$ of the amine (Table 1). Each amine has a different $pK_a$ and interacts with polyaniline differently. Ethylene diamine is the most basic of the amines listed and therefore does not dope polyaniline well resulting in a film with a very high initial resistance. Metanilic acid is the most acidic of the amines listed and dopes polyaniline well. These differences in pKa affect the initial resistance of the composite films and as a result affect the response of the film to phosgene. The hydrochloric acid salts of the amines dissociate in water to generate HCl that partially dopes the polyaniline nanofibers resulting in lower initial resistances than the pure amines. It should be understood that the principles described herein are not limited to polyaniline nanofiber materials and, for example, are applicable to conducting polymer materials in general. Other examples of conducting polymers are polypyrrole, polythiophene, etc.

Figure 5:
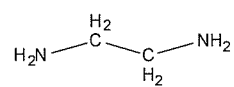
FIG. 5 shows example chemical structures of the amines.
Figure 5:
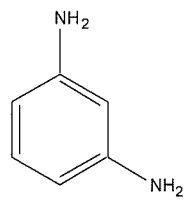
Figure 5:
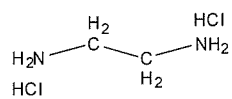
Figure 5:
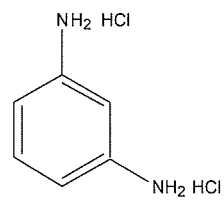
Figure 5:
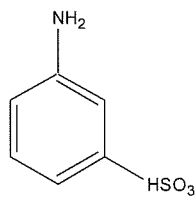

In addition to $pK_a$, the structure of the amine also affects the response of the film to phosgene. FIG. 5 shows the chemical structure of the amines. Ethylene diamine is the smallest amine and can easily react with phosgene. Phenylene diamine is larger with benzene groups that may decrease the interaction of phosgene with the amine causing a smaller response than ethylene diamine.

TABLE 1

$pK_a$ of amines.

| Amine | $pK_a$ |
|---|---|
| Ethylene Diamine | 9.92 |
| m-Phenylene Diamine | 5.11 |
| Metanilic Acid | 3.74 |

The sensing technique described above facilitates extremely sensitive phosgene detection, an example chemical sensor implementation being capable of detecting phosgene well below the Permissible Exposure Limit (PEL) of 100 ppb. Potential uses include, but are not limited to, homeland security, industrial safety and process monitoring.

Figure 6:
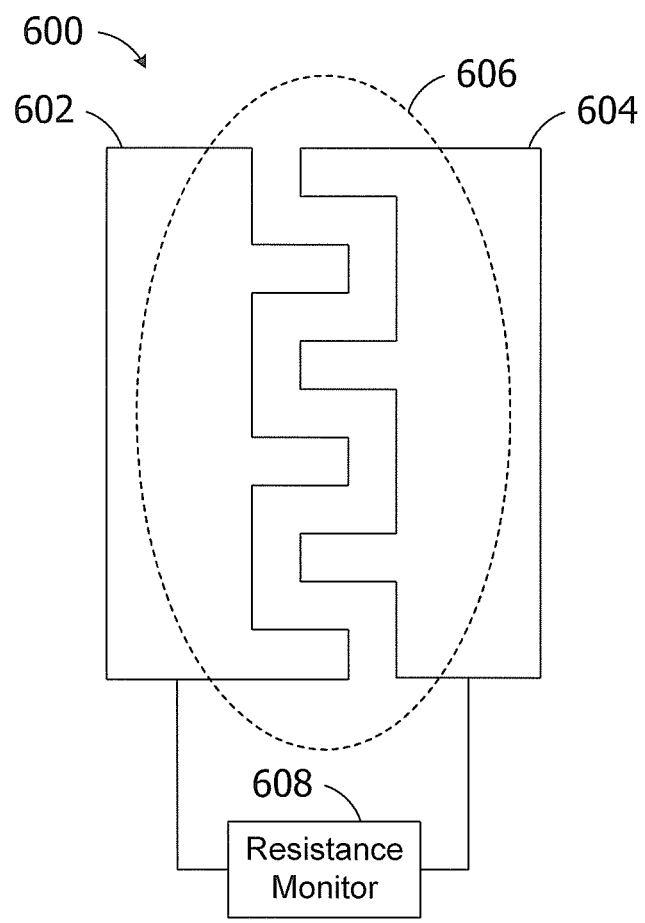
FIG. 6 illustrates an example embodiment of a phosgene sensor including polyaniline nanofiber-amine composite material.

Referring to FIG. 6, in an example embodiment, a sensor 600 includes a pair of electrodes 602 and 604, and a layer 606 of amine modified polyaniline material (shown in dashed lines) positioned over and contacting the electrodes 602 and 604. In this example embodiment, the electrodes 602 and 604 are interdigitated as shown. The electrodes 602 and 604 are formed of a conductive material, such as gold. As noted above, in an example embodiment, the gap between the electrodes is approximately 20 µm.

In this example embodiment, the sensor 600 also includes a resistance monitor 608 connected across the electrodes 602 and 604 for measuring the resistance of the layer 606 of amine modified polyaniline material as it changes in response to the amine modified polyaniline material being exposed to phosgene.

Although the present invention has been described in terms of the example embodiments above, numerous modifications and/or additions to the above-described embodiments would be readily apparent to one skilled in the art. It is intended that the scope of the present invention extend to all such modifications and/or additions.

What is claimed is:

1. A phosgene sensor, the sensor comprising:
a pair of electrodes separated by an electrode gap; and
a layer of conducting polymer material positioned over and making electrical contact with each of the pair of electrodes, the layer of conducting polymer material having been exposed to an aqueous solution of an amine to provide an amine modified conducting material such that the electrical resistance of the amine modified conducting polymer material when measured across the electrodes is responsive to the presence of phosgene and changes depending on an amount of phosgene to which the amine modified conducting polymer material is exposed.

2. The sensor of claim 1, further comprising:
a resistance monitor electrically connected across the electrodes.

3. The sensor of claim 1, wherein the electrodes are interdigitated.

4. The sensor of claim 1, wherein the electrodes are made of gold.

5. The sensor of claim 1, wherein the electrode gap is approximately 20 µm.

6. The sensor claim 1, wherein the conducting polymer is polyaniline, polypyrrole, or polythiophene.

7. The sensor of claim 1, wherein the conducting polymer material includes nanofibers.

8. The sensor of claim 1, wherein the conducting polymer material is a film.

9. The sensor of claim 1, wherein the amine is water soluble.

10. The sensor of claim 1, wherein the amine is ethylene diamine.

11. The sensor of claim 1, wherein the amine is ethylene diamine dihydrochloride salt.

12. The sensor of claim 1, wherein the amine is phenylene diamine.

13. The sensor of claim 1, wherein the amine is phenylene diamine dihydrochloride salt.

14. The sensor of claim 1, wherein the amine is metanilic acid.

15. A phosgene sensor, the sensor comprising:
    a pair of electrodes comprising a first and a second electrode separated by a gap; and
    a polyaniline nanofiber composite material positioned over the gap and making electrical contact with each of the pair of electrodes, the polyaniline nanofiber composite material having been exposed to an aqueous solution of an amine additive to provide an amine modified polyaniline exposed to an aqueous solution of an amine additive to provide an amine modified polyaniline nanofiber composite material such that the electrical resistance of the amine modified polyamiline nanofiber composite material measured across the electrodes is responsive to changes in an amount of phosgene to which the amine modified polyniline nanofiber composite material is exposed.

16. The sensor of claim 15, further comprising:
    a resistance monitor electrically connected across the electrodes.

17. The sensor of claim 15, wherein the electrodes are interdigitated.

18. The sensor of claim 15, wherein the electrodes are made of gold.

19. The sensor of claim 15, wherein the electrode gap is approximately 20 μm.

20. The sensor of claim 15, wherein the polyaniline material is a film.

21. The sensor of claim 15, wherein the amine additives include a water soluble component.

22. The sensor of claim 15, wherein the amine additives include ethylene diamine.

23. The sensor of claim 15, wherein the amine additives include ethylene diamine dihydrochloride salt.

24. The sensor of claim 15, wherein the amine additives include phenylene diamine.

25. The sensor of claim 15, wherein the amine additives include phenylene diamine dihydrochloride salt.

26. The sensor of claim 15, wherein the amine additives include metanilic acid.

* * * * *